US011975087B2

(12) United States Patent
Fan et al.

(10) Patent No.: US 11,975,087 B2
(45) Date of Patent: May 7, 2024

(54) SULFATE-FREE PERSONAL CARE COMPOSITIONS AND METHODS FOR PREVENTING AND TREATING POLLUTION DAMAGE TO SKIN

(71) Applicant: COLGATE-PALMOLIVE COMPANY, New York, NY (US)

(72) Inventors: Aixing Fan, Bridfewater, NJ (US); Nadia Soliman, East Brunswick, NJ (US); Thomas Boyd, Metuchen, NJ (US); Amira Khan, East Windsor, NJ (US); Hayoun Jung, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/834,589

(22) Filed: Mar. 30, 2020

(65) Prior Publication Data
US 2021/0299016 A1 Sep. 30, 2021

(51) Int. Cl.
A61K 8/41 (2006.01)
A61K 8/81 (2006.01)
A61Q 17/00 (2006.01)

(52) U.S. Cl.
CPC ............ A61K 8/416 (2013.01); A61K 8/8111 (2013.01); A61Q 17/00 (2013.01)

(58) Field of Classification Search
CPC ................................ A61Q 17/10; A61Q 19/10
See application file for complete search history.

(56) References Cited

U.S. PATENT DOCUMENTS

| 5,443,817 | A | * | 8/1995 | Zimmerman | ............ | A61Q 1/14 424/47 |
| 7,157,413 | B2 | | 1/2007 | Lazzeri et al. | | |
| 7,326,775 | B2 | | 2/2008 | Naidu | | |
| 7,928,087 | B2 | | 4/2011 | Fack et al. | | |
| 8,343,902 | B2 | | 1/2013 | Walters et al. | | |
| 9,271,908 | B2 | | 3/2016 | Allef et al. | | |
| 9,320,697 | B2 | | 4/2016 | Kleinen et al. | | |
| 9,877,906 | B2 | | 1/2018 | Doi et al. | | |
| 9,949,915 | B2 | | 4/2018 | Rubin et al. | | |
| 9,993,408 | B2 | | 6/2018 | Fevola et al. | | |
| 10,561,592 | B2 | | 2/2020 | Darras et al. | | |
| 10,695,285 | B2 | | 6/2020 | Leclere | | |
| 2004/0057874 | A1 | | 3/2004 | Ishiguro | | |
| 2008/0187502 | A1 | | 8/2008 | Garay et al. | | |
| 2013/0017243 | A1 | * | 1/2013 | Shi | ..................... | A61K 31/4025 604/93.01 |
| 2015/0313827 | A1 | * | 11/2015 | Hardy | ..................... | A61K 8/27 424/59 |
| 2017/0319453 | A1 | | 11/2017 | Ando | | |
| 2018/0016524 | A1 | * | 1/2018 | Dong | ..................... | A61K 8/466 |
| 2018/0098923 | A1 | | 4/2018 | Hutton, III | | |
| 2018/0311127 | A1 | | 11/2018 | Padyachi et al. | | |
| 2019/0000902 | A1 | | 1/2019 | Leclere-Bienfait et al. | | |
| 2019/0021971 | A1 | | 1/2019 | Schroeder et al. | | |
| 2019/0262248 | A1 | | 8/2019 | Youssef et al. | | |
| 2019/0365623 | A1 | | 12/2019 | Botto et al. | | |

FOREIGN PATENT DOCUMENTS

| EP | 1353631 | 9/2011 |
| EP | 2468842 | 6/2012 |
| EP | 2277860 | 8/2015 |
| EP | 2932959 | 10/2015 |
| EP | 3061442 | 8/2016 |
| EP | 3260171 | 12/2017 |
| FR | 3029778 | 6/2016 |
| WO | 2015/079026 | 6/2015 |
| WO | 2016/092189 | 6/2016 |
| WO | 2019/170249 | 9/2019 |
| WO | 2019/193109 | 10/2019 |
| WO | 2020/023187 | 1/2020 |

OTHER PUBLICATIONS

Rembiesa et al. "The impact of pollution on skin and proper efficacy testing for anti-pollutions claims", Cosmetics 2018, 5, 4; doi; 10.3390/ cosmetics 5010004. (Year: 2018).*
Pluracare L/F Grades Poloxamer: Technical Information, BASF, Jul. 2009.*
Bio-Terge As-40, Product Bulletin, Stepan, Aug. 2012.*
Handbook of Detergents, CRC Press, (2009 by Uri Zoller), pp. 287-293.*
Bioelements, USA, 2019, "Urban Undo Cleanser", Mintel Database GNPD AN: 6889243.
Change Look, 2018, "Botanic Active Gel", Mintel Database GNPD AN: 6044749.
International Search Report and the Written Opinion of the International Searching Authority issued in International Application PCT/US2021/024692 dated Jul. 19, 2021.

(Continued)

Primary Examiner — Gina C Justice

(57) ABSTRACT

Personal care compositions and methods for treating or preventing lipid peroxidation of skin with the same are disclosed. The personal care composition may include a carrier and a surfactant system present in an effective amount to treat or prevent lipid peroxidation of skin. The surfactant system may include at least one amphoteric surfactant and at least one anionic surfactant. The method may include contacting the personal care composition with the skin and exposing the skin to pollution. Methods for formulation a personal care composition for treating or preventing lipid peroxidation of skin are also disclosed. The method may include determining an oxidation protection factor (OPF) of one or more components, using the OPF to select at least one component of the one or more components, and combining the at least one component of the one or more components with a carrier to form the personal care composition.

13 Claims, No Drawings

(56) References Cited

OTHER PUBLICATIONS

International Search Report and the Written Opinion of the International Searching Authority issued in International Application PCT/US2021/070333 dated Jul. 27, 2021.
Productos Familia, 2019, "Intimate Soap," Mintel Database GNPD AN: 6915113.
Pendergrass, K. et al., "Should Xanthan Gum be allowed in Grain-Free, Paleo, and Keto Certified Standards?" Microbiome Diet Research, (Dec. 2019) The Paleo Foundation Research Review, pp. 1-11.
Niziol-Lukaszewska Z et al.: "Inulin as an Effectiveness and Safe Ingredient in Cosmetics", Polish Journal of Chemical Technology, 2019, vol. 21, No. 1, pp. 44-49, DOI: 10.2478/ pjct-2019-0008.

* cited by examiner

SULFATE-FREE PERSONAL CARE COMPOSITIONS AND METHODS FOR PREVENTING AND TREATING POLLUTION DAMAGE TO SKIN

BACKGROUND

Signs of aging often appear on skin as fine lines and wrinkles, age spots, dryness, blotchy discolorations, and sagging. Similarly, signs of aging may also manifest in hair as frizziness, dullness, and hair loss. These signs of aging or damage to the skin and hair are often exacerbated by other factors, such as environmental or extrinsic factors. For example, signs of aging or damage to the skin and hair may often be accelerated by exposure to environmental pollution, ultraviolet radiation, ozone, free radicals, or the like. As such, there is a continuing need for personal care compositions and methods for treating and/or preventing damage to the skin and hair.

In addition to concerns regarding exposure of skin and hair to environmental pollution, there is an increasing consumer demand for personal care compositions that incorporate milder surfactants or that are free of sulfate-containing surfactants as these surfactants may often be associated with skin and/or eye irritation. For example, sulfate containing surfactants may often strip the skin and hair of its natural oils, thereby leading to over-drying of skin and hair. As such, there is continuing demand for personal care compositions that are free of sulfate-containing surfactants, such as sodium lauryl sulfate (SLS), ammonium lauryl sulfate (ALS), sodium laureth sulfate (SLES), and ammonium laureth sulfate (ALES).

What is needed, then, are sulfate-free personal care compositions and methods for preventing and treating pollution damage to skin.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care composition including a carrier and a surfactant system. The surfactant system may be present in an amount effective to treat or prevent lipid peroxidation of skin. The surfactant system may include at least one amphoteric surfactant and at least one anionic surfactant.

In at least one implementation, the at least one amphoteric surfactant may include at least one quaternary ammonium group and at least one carboxylate.

In at least one implementation, the at least one amphoteric surfactant may include a betaine-based surfactant, preferably, the betaine-based surfactant may include one or more of cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, lauryl-bis-(2-hydroxypropyl)-carboxyethyl betaine, or combinations thereof, more preferably the betaine-based surfactant includes cocamidopropyl betaine.

In at least one implementation, the at least one anionic surfactant may include an alpha olefin sulfonate, wherein the alpha olefin sulfonate may include from about 8 to about 20 carbon atoms per molecule, more preferably from about 14 to about 16 carbon atoms per molecule.

In at least one implementation, the at least one anionic surfactant may include sodium alpha olefin sulfonate.

In at least one implementation, the at least one amphoteric surfactant may be present in an amount of from about 1 weight % to about 11 weight %, about 5 weight % to about 7 weight %, or more preferably about 6 weight %, based on a total weight of the personal care composition.

In at least one implementation, the at least one anionic surfactant may be present in an amount of from about 1 weight % to about 6 weight %, about 2 weight % to about 5 weight %, or preferably about 3 weight % to about 4 weight %, based on a total weight of the personal care composition.

In at least one implementation, the at least one amphoteric surfactant and the at least one anionic surfactant may be present in a weight ratio of from about 0.5:1 to about 3:1, about 1.5:1 to about 2:1, more preferably about 1.7:1.

In at least one implementation, the surfactant system may be present in an amount of from about 2 weight % to about 20 weight %, about 4 weight % to about 16 weight %, preferably about 8 weight % to about 12 weight %, more preferably about 10 weight %, based on a total weight of the personal care composition.

In at least one implementation, the personal care composition may consist essentially of the carrier and the surfactant system, and the surfactant system may consist essentially of the at least one amphoteric surfactant and the at least one anionic surfactant.

In at least one implementation, the personal care composition may consist of the carrier and the surfactant system, and the surfactant system may consist of the at least one amphoteric surfactant and the at least one anionic surfactant.

In at least one implementation, the carrier may include a thickener. The thickener may include a polymer, preferably the polymer is a poloxamer, more preferably the poloxamer is a poly(ethylene glycol)-poly(propylene glycol)-poly(ethylene glycol) block copolymer (PEG-PPG-PEG).

In at least one implementation, the personal care composition may be free of any one or more of sodium lauryl sulfate (SLS), ammonium lauryl sulfate (ALS), sodium laureth sulfate (SLES), ammonium laureth sulfate (ALES), or combinations thereof. In one example, the personal care composition is free of any sulfate-containing surfactants.

In at least one implementation, wherein the personal care composition may be free of coco-glucoside, salt thickeners, or combinations thereof.

In at least one implementation, the personal care composition may have a pH of from about 3.5 to about 5.5, about 4 to about 5, preferably about 4.5.

The foregoing and/or other aspects and utilities embodied in the present disclosure may be achieved by providing a method for preparing the personal care composition of any one or more of the personal care compositions disclosed herein. The method may include contacting the carrier and the surfactant with one another.

The foregoing and/or other aspects and utilities embodied in the present disclosure may be achieved by providing a method for treating or preventing lipid peroxidation of skin. The method may include contacting any one or more of the personal care compositions disclosed herein with the skin, and exposing the skin to pollution. The personal care composition may prevent lipid peroxidation of the skin.

The foregoing and/or other aspects and utilities embodied in the present disclosure may be achieved by providing a method for formulating a personal care composition for treating or preventing lipid peroxidation of skin. The method may include determining an oxidation protection factor (OPF) of one or more components. The method may also include using the OPF to select as least one component of the one or more components. The method may further include combining the at least one component of the at least one or more components with a carrier to form the personal care composition.

The foregoing and/or other aspects and utilities embodied in the present disclosure may be achieved by providing a method for predicting the efficacy of a personal care composition for treating or preventing pollution damage to skin. The method may include contacting the personal care composition with an in-vitro skin model, and measuring an amount of a byproduct of lipid peroxidation present in the in-vitro skin model, wherein the byproduct of lipid peroxidation includes a malondialdehyde (MDA). The method may also include determining an oxidation protection factor (OPF) with the amount of the MDA present in the in-vitro skin model. The OPF may predict the efficacy of the personal care composition for treating or preventing pollution damage to skin.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that personal care compositions including a carrier and a surfactant system including at least one amphoteric surfactant and at least one anionic surfactant prevents pollution damage or lipid peroxidation in and/or on skin when applied to the skin prior to exposure to ozone. Particularly, the inventors have surprisingly and unexpectedly discovered that personal care compositions including a carrier and a surfactant system including at least one amphoteric surfactant, such as a betaine-based surfactant, and at least one anionic surfactant, such as an alpha olefin sulfonate, prevents pollution damage or lipid peroxidation in and/or on skin when applied to the skin prior to exposure to ozone. The betaine-based surfactant may be cocamidopropyl betaine, and the alpha olefin sulfonate may be sodium (C14-C16) olefin sulfonate. The amphoteric surfactant, preferably cocamidypropyl betaine, and the anionic surfactant, preferably sodium (C14-C16) olefin sulfonate, may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

The present inventors have also surprisingly and unexpectedly discovered that personal care compositions including a carrier and a surfactant system including at least one amphoteric surfactant and at least one anionic surfactant reduces, removes, or otherwise treats pollution damage or lipid peroxidation in and/or on skin when applied to the skin after exposure to ozone. Particularly, the inventors have surprisingly and unexpectedly discovered that personal care compositions including a carrier and a surfactant system including at least one amphoteric surfactant, such as a betaine-based surfactant, and at least one anionic surfactant, such as an alpha olefin sulfonate, reduces, removes, or treats pollution damage or lipid peroxidation in and/or on skin when applied to the skin after exposure to ozone. The betaine-based surfactant may be cocamidopropyl betaine, and the alpha olefin sulfonate may be sodium (C14-C16) olefin sulfonate. The amphoteric surfactant, preferably cocamidopropyl betaine, and the anionic surfactant, preferably sodium (C14-C16) olefin sulfonate, may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Compositions

Compositions disclosed herein may be or include a personal care product or a personal care composition thereof. For example, compositions disclosed herein may be a personal care composition, a personal care product, or form a portion of the personal care composition or the personal care product. In an exemplary implementation, the compositions disclosed herein are personal care composition including a carrier and an effective amount of a surfactant system including at least one amphoteric surfactant and at least one anionic surfactant. The carrier may be capable of or configured to store, entrain, or otherwise contain the surfactant system, and deliver the surfactant system to one or more tissues, such as skin. The surfactant system may be capable of or configured to prevent pollution damage or lipid peroxidation in and/or on skin when applied to the skin prior to exposure to ozone. The surfactant system may also be capable of or configured to reduce, remove, or treat pollution damage or lipid peroxidation in and/or on skin when applied to the skin after exposure to ozone. As further described herein, the amphoteric surfactant and the anionic surfactant may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Illustrative personal care products or compositions thereof that may include the carrier and the surfactant system may include, but are not limited to, body washes, shower gels, so liquid soaps, face washes, shampoos, hair conditioners, lotions, moisturizers, serums, or the like. In a preferred implementation, the personal care product or the composition thereof that includes the carrier and the surfactant system are liquid cleansing compositions, such as shower gels.

The surfactant system of the personal care composition may include one or more surfactants. The one or more surfactants may be or include, one or more anionic surfactants, one or more nonionic surfactants, one or more cationic surfactants, one or more amphoteric or zwitterionic surfactants, or combinations thereof. In a preferred implementation, the personal care composition includes at least one amphoteric surfactant and at least one anionic surfactant. The at least one amphoteric surfactant and the at least one anionic surfactant may be capable of or configured to prevent, treat, and/or reduce/remove pollution damage or lipid peroxidation in skin when contacted therewith. For example, the personal care composition including the combination of the amphoteric surfactant and the anionic surfactant may be capable of or configured to prevent, treat, and/or remove pollution damage or lipid peroxidation in skin when contacted therewith.

In at least one implementation, the personal care composition includes at least one amphoteric surfactant including at least one quaternary ammonium group or cation and at least one carboxylate. For example, the at least one amphoteric surfactant may be or include, but is not limited to, a betaine-based surfactant. Illustrative betaine-based surfactants may be or include, but are not limited to, imidazoline-based betaines, alkyl dimethyl aminoacetic acid betaines, fatty acid amide propyl betaines, sulfobetaines, or combinations thereof. In a preferred implementation, the betaine-based surfactant may be or include one or more fatty acid amide propyl betaines or fatty acid amidopropyl betaines. Illustrative betaine-based surfactants may be or include, but are not limited to, cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, lauryl-bis-(2-hydroxypropyl)-carboxyethyl betaine, or the like, or combinations thereof. In a preferred embodiment, the betaine-based surfactant includes cocamidopropyl betaine.

The one or more amphoteric surfactants may be present in an amount of from about 1 weight % to about 11 weight %, based on a total weight of the personal care composition. For example, the one or more amphoteric surfactants may be present in an amount of from 1 weight %, about 3 weight %, or about 5 weight % to about 7 weight %, about 9 weight %, or about 11 weight %, based on a total weight of the personal care composition. In a preferred implementation, the one or more amphoteric surfactants may be present in an amount of from about 1 weight % to about 11 weight %, about 3 weight % to about 9 weight %, preferably from about 5 weight % to about 7 weight %, or more preferably about 6 weight %, based on a total weight of the personal care composition.

In at least one implementation, the personal care composition may include at least one anionic surfactant. The at least one anionic surfactant may include one or more of the following anionic surfactants: a taurate, a succinate, a sarcosinate, an isethionate, a carboxylate, a lactylate, a glutamate, a glycinate, a sulfoacetate, a sulfonate surfactant, or combinations thereof. Illustrative anionic surfactants may be or include, but are not limited to, sodium n-methyl-n-oleyl taurate, sodium cocoyl isethionate, sodium capryloyl isethionate, sodium caproyl isethionate, sodium lauroyl isethionate, sodium palmitoyl isethionate, sodium diisobutyl sulfosuccinate, sodium diamyl sulfosuccinate, di-N-hexyl sodium sulfosuccinate, disodium lauryl sulfosuccinate, disodium laureth sulfosuccinate, disodium PEG-12 dimethicone sulfosuccinate, sodium oleyl sarcosinate, sodium laurate, sodium myristate, sodium palmitate, sodium stearate, sodium lauroyl lactylate, sodium palmitoyl lactylate, sodium stearoyl lactylate, sodium cocoyl glutamate, disodium cocoyl glutamate, sodium lauroyl glycinate, sodium lauryl sulfoacetate, stearyltoluene sodium sulfonate, sodium diamyl sulfosuccinate, sodium pentanesulfonate, a linear alkyl benzene sulfonate (e.g., sodium dodecylbenzenesulfonate or ammonium dodecylbenzenesulfonate), sodium 1-butanesulfonate, sodium lignosulfonate, sodium n-octyl sulfonate, an alpha olefin sulfonate, or combinations thereof.

In an exemplary implementation, the anionic surfactant may be or include one or more sulfonate surfactants. In a preferred implementation, the at least one anionic surfactant includes an alpha olefin sulfonate (AOS). The alpha olefin sulfonate may include from about 8 to about 20 carbon atoms per molecule (C8-C20), about 10 to about 18 carbon atoms per molecule (C10-C18), about 12 to about 18 carbon atoms per molecule (C12-C18), or more preferably from about 14 to about 16 carbon atoms per molecule (C14-C16). In at least one implementation, the alpha olefin sulfonate is sodium alpha olefin sulfonate. The anionic surfactant may interact or form a complex with the amphoteric surfactant. For example, the betaine-based surfactant, such as cocamidopropyl betaine, may interact or complex with the anionic surfactant, such as alpha olefin sulfonate.

The one or more anionic surfactants may be present in an amount of from about 1 weight % to about 5 weight %, based on a total weight of the personal care composition. For example, the one or more anionic surfactants may be present in an amount of from about 1 weight %, about 2 weight %, or about 3 weight % to about 4 weight %, about 5 weight %, or about 6 weight %, based on a total weight of the personal care composition. In a preferred implementation, the one or more anionic surfactants may be present in an amount of from about 1 weight % to about 6 weight %, about 2 weight % to about 5 weight %, preferably from about 3 weight % to about 4 weight %, or more preferably about 3.5 weight %, based on a total weight of the personal care composition.

In a preferred implementation, the personal care composition includes at least one amphoteric surfactant and at least anionic surfactant. For example, the personal care composition or a surfactant system thereof includes at least one amphoteric surfactant and at least anionic surfactant. In a preferred implementation, the personal care composition or the surfactant system thereof may consist essentially of at least one amphoteric surfactant and at least anionic surfactant. The at least one amphoteric surfactant may be or include cocamidopropyl betaine, and the at least one anionic surfactant may be or include sodium (C14-C16) alpha olefin sulfonate. For example, the personal care composition or the surfactant system thereof may include at least one amphoteric surfactant, such as cocamidopropyl betaine, at least one anionic surfactant, such as sodium (C14-C16) alpha olefin sulfonate, and may further include any one or more additional surfactants that do not materially affect the ability of the personal care composition for preventing and/or treating pollution in and/or on skin. For example, the personal care composition or the surfactant system thereof may include a combination of cocamidopropyl betaine, sodium (C14-C16) alpha olefin sulfonate, and any additional surfactants that do not materially affect the ability of the personal care composition for preventing and/or treating lipid peroxidation in and/or on skin. In another implementation, the personal care composition or the surfactant system thereof may consist of cocamidopropyl betaine and sodium (C14-C16) alpha olefin sulfonate.

The at least one amphoteric surfactant and the at least one anionic surfactant may be present in a weight ratio of from about 0.5:1 to about 3:1. For example, the amphoteric surfactant and the anionic surfactant may be present in a weight ratio of from about 0.5:1 to about 3:1, about 1:1 to about 2.5:1, about 1.5:1 to about 2:1, or about 1.7:1. In a preferred implementation, the weight ratio of the amphoteric surfactant to the anionic surfactant may be from about 1.5:1 to about 2:1, more preferably about 1.7:1.

In at least one implementation, the personal care composition may be free or substantially free of sulfate-containing surfactants. Illustrative sulfate-containing surfactants may be or include, but are not limited to, sodium lauryl sulfate (SLS), ammonium lauryl sulfate (ALS), sodium laureth sulfate (SLES), ammonium laureth sulfate (ALES), or the like. The personal care composition may also be free or substantially free of one or more alkylglucosides. Illustrative alkyl glucosides may be or include, but are not limited to, capryl glucoside, decyl glucoside, coco-glucoside, lauryl glucoside, or the like, or combinations thereof. In a preferred implementation, the personal care composition is free or substantially free of coco-glucoside and sulfate-containing surfactants.

In at least one implementation, the total amount of surfactants present in the personal care composition may be from about 2 weight % to about 20 weight %, based on a total weight of the personal care composition. For example, the total amount of surfactants present in the personal care composition may be from about 2 weight %, about 4 weight %, or about 8 weight % to about 12 weight %, about 16 weight %, about 18 weight %, or about 20 weight %, based on a total weight of the personal care composition. In at least one implementation, the total amount of the surfactants present in the personal care composition may be from about 2 weight % to about 20 weight %, about 4 weight % to about 16 weight %, preferably about 8 weight % to about 12 weight %, or more preferably about 10 weight %, based on a total weight of the personal care composition.

The carrier of the personal care composition may include, but is not limited to, any one or more of fragrances, essential oils, water, emulsifying agents, thickeners, colorants, natural actives, therapeutic actives, stain prevention actives, antimicrobial agents, vitamins, natural extracts, amino acids, enzymes and/or other proteins, abrasives, odor control agents, conditioning agents, moisturizers, humectants, pH modifying agents (e.g., acids, bases, and/or buffers), occlusive agents, skin lipid fluidizers, lipophilic actives, hydrophilic materials, pearlizers, opacifying agents, sodium soaps, titanium dioxide, dyes, preservatives, antioxidants, chelating agents, opacifiers, hydric solvents, hydrotropes, skin care agents, or the like, or any mixture or combination thereof, in addition to any one or more of the other carrier components disclosed herein.

Water of the personal care composition or the carrier thereof may be deionized water, demineralized water, and/or softened water. Water may make up the balance of the personal care composition For example, the amount of water in the personal care composition may be from about 10 wt % to 90 wt %, about 40 wt % to about 85 wt %, or about 60 wt % to about 80 wt %. In another example, the amount of water in the personal care composition may be at least 60 wt %, at least 65 wt %, at least 70 wt %, at least 72 wt %, at least 74 wt %, at least 76 wt %, at least 78 wt %, or at least 79 wt %. The amount of water in the personal care composition may include free water added and water introduced with other components or materials of the personal care composition. For example, the amount of the water in the liquid cleansing composition may include free water and water associated with the surfactants or any other component of the personal care composition.

In at least one implementation, the personal care composition or the carrier thereof may include one or more humectants. Illustrative humectants may be or include, but are not limited to, glycerin, propylene glycol, polyethylene glycol, ascorbic acid, ascorbyl dipalmitate, acetamide MEA, caprylyl glycol, glucose glutamate, glucuronic acid, TEA-lactate, TEA-PCA, corn syrup, fructose, glucose, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, or the like, or combinations thereof. In a preferred implementation, the humectants may be or include, but is not limited to, glycerin.

In at least one implementation, the personal care composition may include a thickener or thickening agent capable of or configured to modify (e.g., increase or decrease) a viscosity of the personal care composition. In at least one implementation, the thickener may include a polymer, such as a poloxamer. The poloxamer may be a liquid or a paste. The poloxamer may be or include a block copolymer. For example, the poloxamer may be or include a poly(ethylene glycol)-poly(propylene glycol)-poly(ethylene glycol) block copolymer (PEG-PPG-PEG), such as, poly(ethylene glycol)-block-poly(propylene glycol)-block-poly(ethylene glycol). The poloxamer may have an average molecular weight of less than or equal to about 12,000 Dalton (Da), less than or equal to about 11,000 Da, less than or equal to about 10,000 Da, less than or equal to about 9,000 Da, less than or equal to about 8,000 Da, less than or equal to about 7,000 Da, or less than or equal to about 6,000 Da. Illustrative poloxamers may be or include, but are not limited to, one or more of PLURONIC® L35, PLURONIC® L43, PLURONIC® L64, PLURONIC® L10, PLURONIC® L44 (CAS No. 9003-11-6), PLURONIC® L62, PLURONIC® 10R5, PLURONIC® 17R4, PLURONIC® L25R4, PLURONIC® P84, PLURONIC® P65, PLURONIC® P104, and PLURONIC® P105, or the like, or any mixture or combination thereof, each of which or commercially available from BASF Corp. of Florham Park, N.J. In a preferred implementation, the polymer includes poloxamer 124 or PLURONIC® L44 (CAS No. 9003-11-6).

As discussed above, in at least one implementation, the personal care composition or the surfactant system thereof may include at least one amphoteric surfactant, such as cocamidopropyl betaine, and at least one anionic surfactant, such as sodium (C14-C16) alpha olefin sulfonate. In such an implementation, the personal care composition may utilize the polymer, such as the poloxamer, as the thickener, in lieu of a salt as the thickener, as the salt may be ineffective as a thickener in a surfactant system including an anionic surfactant, such as sodium (C14-C16) alpha olefin sulfonate. As such, in at least one preferred implementation, the personal care composition may be free or substantially free of salt utilized as a thickener.

In at least one implementation, the personal care composition may include one or more acids, one or more bases, and/or one or more buffers or buffering agents configured to adjust or control the pH of the personal care composition. The one or more acids, one or more bases, and/or one or more buffers may, separately and independently, be present in an amount of from greater than 0 weight % to less than or equal to about 10 weight %, less than or equal to about 8 weight %, less than or equal to about 6 weight %, less than or equal to about 4 weight %, less than or equal to about 2 weight %, less than or equal to about 1 weight %, or less than or equal to about 0.5 weight %, based on a total weight of the personal care composition or the hydrophilic phase thereof. Illustrative bases may include, but are not limited to, ammonia; mono-, di-, and tri-alkyl amines; mono-, di-, and tri-alkanolamines; alkali metal and alkaline earth metal hydroxides; sodium hydroxide, potassium hydroxide, lithium hydroxide, monoethanolamine, triethylamine, isopropanolamine, diethanolamine, triethanolamine, or the like, or combinations thereof. Illustrative acids may include, but are not limited to, mineral acids, such as hydrochloric acid, nitric acid, phosphoic acid, and sulfuric acid, organic acids, polycarboxylic and/or organic acids, such as citric acid, acetic acid, lactic acid, glycolic acid, formic acid, butyric acid, propionic acid, valeric acid, malic acid, oxalic acid, carbonic acid, taurine, or the like, or combinations thereof. In a preferred implementation, the personal care composition includes at least one organic acid, such as lactic acid, present in an amount of from greater than 1 weight % to about 6 weight %, from about 3 weight % to about 5 weight %, or about 4 weight %, based on a total weight of the personal care composition. It should be appreciated that, in addition to modifying the pH of the personal care composition, lactic acid may also provide one or more additional benefits to the personal care composition. For example, the lactic acid may stimulate natural moisturizing factors (NMFs) in skin and provide whitening benefits to skin.

The personal care composition may have a neutral pH, an alkaline pH, or an acidic pH. In a preferred embodiment, the personal care composition is acidic. For example, the personal care composition may have a pH less than 7. In another example, the personal care composition may have a pH greater than or equal to 3 and less than 7. For example, the personal care composition may have a pH of from about 3, about 3.5, about 4, or about 4.5 to about 5, about 5.5, or about 6. In another example, the personal care composition may have a pH of from about 3 to less than 7, about 3.5 to about 5.5, about 4 to about 5, or about 4.5. In a preferred embodiment, the personal care composition has a pH of from about 4 to about 5, or about 4.5.

In some implementation, the personal care composition may include one or more skin care agents. Any suitable skin care agents that do not adversely affect the stability and/or efficacy of the personal care composition may be used. In at least one implementation, the skin care agent may include one or more emollients configured to maintain a soft, smooth, and pliable appearance to the skin. As is known by those skilled in the art, the emollients may function by remaining on the surface of the skin or in the stratum corneum to act as a lubricant, to reduce flaking, and/or to improve the appearance of the skin.

The skin care agents may generally include one or more starches (e.g., tapioca starches, hydrophobically modified corn starch, such as DRY-FLO TS® CAS Nos. 68989-12-8, 68554-70-1, 9005-25-8, etc.), protein derivatives (e.g., derivatized hydrolyzed wheat protein), ethoxylated fatty ethers, cellulosics (e.g., hydroxyethylcellulose), or the like, or combinations thereof. Illustrative skin care agents may include, but are not limited to, esters comprising an aliphatic alcohol having about 2 to about 18 carbon atoms condensed with an aliphatic or aromatic carboxylic acid including about 8 to about 20 carbon atoms (e.g., isopropyl myristate, decyl oleate, cetearyl isononanate, etc.). The esters may be straight chained or branched. In a preferred implementation, the ester has a molecular weight of less than about 500.

Other skin care agents may include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, iso-ceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, palmitamidopropyltrimonium chloride, or the like, or combinations thereof. In a preferred implementation, the skin care agent is or includes a conditioner, such as a cationic cellulose polymer, preferably polyquaternium-7.

Unless otherwise specifically identified, the ingredients for use in the compositions and formulations of the compositions disclosed herein are preferably cosmetically acceptable ingredients. As used herein, the expression "cosmetically acceptable" may refer to a component or ingredient that is suitable for use in a formulation for topical application to human skin. A cosmetically acceptable excipient, may refer to an excipient that is suitable for external application in the amounts and concentrations contemplated in the formulations of the compositions disclosed herein, and includes for example, excipients which are "Generally Recognized as Safe" (GRAS) by the United States Food and Drug Administration (FDA).

Methods

Method for Preparing a Personal Care Product/Composition

The present disclosure may provide methods for preparing a personal care product or a personal care composition thereof. The method may include mixing, stirring, combining, or otherwise contacting a carrier and a surfactant system including at least one amphoteric surfactant and at least one anionic surfactant with one another. The least one amphoteric surfactant may be a betaine-based surfactant, and the at least one anionic surfactant may be an alpha olefin sulfonate. In a preferred implementation, the betaine-based surfactant may be cocamidopropyl betaine, and the alpha olefin sulfonate may be sodium (C14-C16) olefin sulfonate. The surfactant system or the surfactants thereof may be present in an effective amount to prevent pollution damage or lipid peroxidation in and/or on skin when applied to the skin prior to exposure to ozone. The surfactant system or the surfactants thereof may also be present in an effective amount to reduce, remove, or treat pollution damage or lipid peroxidation in and/or on skin when applied to the skin after exposure to ozone. The amphoteric surfactant and the anionic surfactant may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Method for Preventing Pollution Damage to Skin

The present disclosure may also provide methods for preventing pollution damage or lipid peroxidation in and/or on skin. For example, the method may include reducing the rate of lipid peroxidation of skin over time. The method may include contacting any one or more of the personal care compositions disclosed herein with the skin prior to exposing the skin to pollution, such as ozone. For example, the method may include contacting a personal care composition including a carrier and a surfactant system including at least one amphoteric surfactant and at least one anionic surfactant with skin. The least one amphoteric surfactant may be a betaine-based surfactant, and the at least one anionic surfactant may be an alpha olefin sulfonate. In a preferred implementation, the betaine-based surfactant may be cocamidopropyl betaine, and the alpha olefin sulfonate may be sodium (C14-C16) olefin sulfonate. The surfactant system or the surfactants thereof may be present in an effective amount to prevent pollution damage or lipid peroxidation in and/or on skin when applied to the skin prior to exposure to ozone. The amphoteric surfactant and the anionic surfactant may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Method for Reducing or Treating Pollution Damage to Skin

The present disclosure may also provide methods for reducing, removing, or otherwise treating pollution damage or lipid peroxidation in and/or on skin. The method may include contacting any one or more of the personal care compositions disclosed herein with the skin after exposing the skin to pollution, such as ozone. For example, the method may include contacting a personal care composition including a carrier and a surfactant system including at least one amphoteric surfactant and at least one anionic surfactant with skin after exposure to ozone. The at least one amphoteric surfactant may be a betaine-based surfactant, and the at least one anionic surfactant may be an alpha olefin sulfonate. In a preferred implementation, the betaine-based surfactant may be cocamidopropyl betaine, and the alpha olefin sulfonate may be sodium (C14-C16) olefin sulfonate. The surfactant system or the surfactants thereof may be present in an effective amount to treat, remove, or otherwise reduce pollution damage or lipid peroxidation in and/or on skin when applied to the skin exposed to pollution. The amphoteric surfactant and the anionic surfactant may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Method for Cleaning Skin and Concurrently Preventing and/or Treating Pollution Damage to Skin The present disclosure may also provide methods for cleansing skin while concurrently preventing and/or treating pollution damage or lipid peroxidation in and/or on skin. The method may include contacting skin with an effective amount of a personal care composition including a carrier and a surfactant system including at least one amphoteric surfactant and at least one anionic surfactant. The least one amphoteric surfactant may be a betaine-based surfactant, and the at least one anionic surfactant may be an alpha olefin sulfonate. In a preferred implementation, the betaine-based surfactant may be cocamidopropyl betaine, and the alpha olefin sulfonate may be sodium (C14-C16) olefin sulfonate. The surfactant system or the surfactants thereof may be present in an effective amount to treat, remove, or otherwise reduce and/or treat pollution damage or lipid peroxidation in and/or on skin when applied to the skin. The amphoteric surfactant and the anionic surfactant may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Personal Care Product/Composition for Use in Preventing Pollution Damage to Skin The present disclosure may also provide a personal care composition for use in preventing pollution damage or lipid peroxidation in and/or on skin. The personal care composition may include a carrier and a surfactant system including at least one amphoteric surfactant, such as a betaine-based surfactant, and at least one anionic surfactant, such as an alpha olefin sulfonate. The betaine-based surfactant may be cocamidopropyl betaine, and the alpha olefin sulfonate may be sodium (C14-C16) olefin sulfonate. The amphoteric surfactant, preferably cocamidypropyl betaine, and the anionic surfactant, preferably sodium (C14-C16) olefin sulfonate, may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Personal Care Product/Composition for Use in Treating Pollution Damage to Skin

The present disclosure may also provide a personal care composition for use in treating pollution damage or lipid peroxidation in and/or on skin. The personal care composition may include a carrier and a surfactant system including at least one amphoteric surfactant, such as a betaine-based surfactant, and at least one anionic surfactant, such as an alpha olefin sulfonate. The betaine-based surfactant may be cocamidopropyl betaine, and the alpha olefin sulfonate may be sodium (C14-C16) olefin sulfonate. The amphoteric surfactant, preferably cocamidopropyl betaine, and the anionic surfactant, preferably sodium (C14-C16) olefin sulfonate, may be present in the personal care composition in a weight ratio of from about 0.5:1 to about 3:1, about 1:1 to about 2.5:1, or preferably about 1.5:1 to about 2:1. The surfactant system or the one or more surfactants thereof may be present in the personal care composition in an amount of from about 4 weight % to about 16 weight %, preferably about 8 weight % to about 12 weight %, or more preferably about 10 weight %, based on a total weight of the personal care composition.

Method for Designing a Personal Care Composition for Treating/Preventing Pollution Damage to Skin The present disclosure may provide a method for designing or formulating a personal care composition capable of or configured to prevent and/or treat pollution damage to skin. The method for designing or formulating a personal care composition may be applied to a personal care composition or one or more components thereof. For example, the method may be applied to a complete personal care composition. In another example, the method may be applied to a single component or a combination of two or more components of the personal care composition.

The method for designing the personal care composition capable of or configured to prevent and/or treat pollution damage to skin may include determining an oxidation or ozone protection factor (OPF) or an oxidation/ozone protection value (OPV) of a personal care composition or one or more components thereof. As used herein, the term or expression "ozone protection factor (OPF)," "ozone protection value (OPV)," or the like, may refer to the efficacy of a composition or one or more components thereof for preventing and/or treating pollution damage to tissue (e.g., skin) or hair. For example, the term or expression "ozone protection factor (OPF)," "ozone protection value (OPV)," or the like, may refer to the efficacy of a composition or one or more components thereof for preventing and/or treating lipid peroxidation in and/or on skin.

The method for designing the personal care composition capable of or configured to prevent and/or treat pollution damage to skin may also include using the OPF to select one or more components of the personal care composition. For example, the method may include categorizing, ordering, grouping, or otherwise organizing the one or more components of the personal care composition by the OPF thereof. For example, the method may include ordering the one or more components of the personal care composition by the OPF either in increasing or decreasing order. In another example, the method may include categorizing each of the one or more components in two or more groups, such as a high OPF group, a middle OPF group, and a low OPF group.

The method for designing the personal care composition capable of or configured to prevent and/or treat pollution damage to skin may also include selecting the one or more components of the personal care composition based on at least the OPF of the respective component. The method may also include combining and/or processing the one or more components of the personal care composition with one another, and/or with one or more additional materials (e.g., carrier) to form a product.

In at least one implementation, determining the OPF may include measuring the amount or degree of lipid peroxidation of skin before and/or after exposure to pollution damage (e.g., exposure to UV, ozone, IR radiation, etc.). Determining the OPF may also include measuring the amount or degree of lipid peroxidation of skin before and/or after treating the skin with a personal care composition or one or more components thereof. The lipid peroxidation of skin may be measured by monitoring or measuring a biomarker and/or a byproduct of lipid peroxidation. For example, lipid peroxidation of skin may be measured by measuring the amount or presence of malondialdehyde (MDA), a byproduct of lipid peroxidation, in and/or on skin.

In at least one implementation, determining the OPF may include measuring the amount of MDA in skin treated with a test personal care composition ($MDA_{TEST}$), measuring the amount of MDA in skin treated with a control personal care composition ($MDA_{CONTROL}$), and applying the ($MDA_{TEST}$) and ($MDA_{CONTROL}$) to formula (1).

$$OPF=[(MDA_{CONTROL})-(MDA_{TEST})]/(MDA_{CONTROL})\times 100 \qquad (1)$$

In at least one implementation, the test personal care composition may include a surfactant system including at least one amphoteric surfactant and at least one anionic surfactant, where the surfactant system is capable of or configured to prevent and/or treat pollution damage or lipid peroxidation in and/or on skin when applied to the skin. In at least one implementation, the control personal care composition may be water or a comparative personal care composition.

The MDA may be measured before and/or after applying and/or rinsing the personal care composition or the one or more components thereof to skin. For example, the MDA may be measured before applying the personal care composition or the one or more components thereof to skin to determine a baseline MDA amount. In another example, the MDA may be measured after applying the personal care composition or the one or more components thereof to skin to measure the effect of applying the personal care composition or the one or more components thereof. The MDA may also be measured before and/or after exposure to pollution damage.

Method for Predicting Efficacy of a Personal Care Composition for Treating/Preventing Pollution Damage to Skin The present disclosure may provide a method to predict the efficacy of a test or exemplary personal care composition for preventing and/or treating skin lipid peroxidation in an in-vitro model. In an exemplary implementation, the personal care composition may be a rinse-off formulation, such as a shower gel. In another implementation, the personal care composition may be a leave-on formulation, such as a lotion.

Method for Predicting Efficacy of a Rinse-Off Personal Care Composition for Treating/Preventing Pollution Damage to Skin The method for predicting the efficacy of a rinse-off personal care composition for preventing and/or treating skin lipid peroxidation in skin may include contacting a test or exemplary rinse-off personal care composition and/or a control rinse-off personal care composition with a respective in-vitro skin model. The method for predicting the efficacy of the rinse-off personal care composition for preventing and/or treating skin lipid peroxidation in an in-vitro model may also include monitoring or measuring a biomarker and/or a byproduct of lipid peroxidation. For example, the method may include measuring the amount or presence of MDA in and/or on skin after contacting the test and/or control rinse-off personal care compositions with the respective in-vitro skin models. As discussed above, the MDA may be extracted from the skin models via a cup scrub method. The method may also include determining the OPF with the amount of MDA extracted and measured from the respective skin models treated with the test and/or control rinse-off personal care compositions.

In at least one implementation, a relatively greater OPF may indicate a relatively greater efficacy of the rinse-off personal care composition for preventing and/or treating lipid peroxidation in and/or on skin. An OPF of from about 50 to about 90 may indicate that the rinse-off personal care composition has a high efficacy for preventing and/or treating skin lipid peroxidation to skin. An OPF of from about 30 to about 50 may indicate that the rinse-off personal care composition has a medium efficacy for preventing and/or treating skin lipid peroxidation to skin. An OPF of of from about 10 to about 30 may indicate that the rinse-off personal care composition has a low efficacy for preventing and/or treating skin lipid peroxidation to skin.

The skin model may be any suitable skin model, such as pig skins. The skin model may be washed and/or rinsed prior to testing. The rinse-off personal care composition may be tested in parallel or with a control rinse-off personal care composition. The control rinse-off personal care composition may be water. In another example, the control rinse-off personal care composition may be a comparative rinse-off personal care composition, such as a comparative commercial rinse-off personal care composition.

To predict the efficacy of the rinse-off personal care composition for preventing lipid peroxidation of skin, the skin models may be contacted with the rinse-off personal care composition, the rinse-off personal care composition may then be rinsed off of the skin models, and the skin models may be subsequently exposed to skin pollution, such as ozone. To predict the efficacy of the rinse-off personal care composition for treating or removing lipid peroxidation of skin, the skin models may be exposed to skin pollution (e.g., ozone), contacted with the rinse-off personal care composition, and subsequently rinsed off of the skin models.

Exposing the skin models to skin pollution may include disposing the skin models in a CH-1 ozone chamber (Model 106-L) commercially available from Oxidation Technologies, LLC. The skin models may be exposed to skin pollution for a time and an amount sufficient to generate MDA in and/or on skin. For example, the skin models may be exposed to about 100 ppb of ozone for about 1 hour to generate MDA.

Contacting the rinse-off personal care composition with the skin may include simulating washing of the skin with the rinse-off personal care composition. For example, contacting the rinse-off personal care composition may include pre-wetting the skin model with water for a predetermined amount of time (e.g., about 2 to about 3 seconds), adding a predetermined amount of the rinse-off personal care composition (e.g., about 200 µL) to the skin model, and producing a lather by rubbing for a predetermined amount of time (e.g., about 15 sec).

Method for Predicting Efficacy of a Leave-On Personal Care Composition for Preventing Pollution Damage to Skin The method for predicting the efficacy of a leave-on personal care composition (e.g., lotion) for preventing skin lipid peroxidation in skin may include contacting a test or exemplary leave-on personal care composition and/or a control leave-on personal care composition with a respective in-vitro skin model. The method for predicting the efficacy of the leave-on personal care composition for preventing skin lipid peroxidation in an in-vitro model may also include monitoring or measuring a biomarker and/or a byproduct of lipid peroxidation. For example, the method may include measuring the amount or presence of MDA in and/or on skin after contacting the test and/or control leave-on personal care compositions with the respective in-vitro skin models. As discussed above, the MDA may be extracted from the skin models via a cup scrub method. The method may also include determining the OPF with the amount of MDA extracted and measured from the respective skin models treated with the test and/or control leave-on personal care compositions.

In at least one implementation, a relatively greater OPF may indicate a relatively greater efficacy of the leave-on personal care composition for preventing and/or treating skin lipid peroxidation in and/or on skin. An OPF of from about 50 to about 90 may indicate that the leave-on personal care composition has a high efficacy for preventing and/or treating skin lipid peroxidation to skin. An OPF of from about 30 to about 50 may indicate that the leave-on personal care composition has a medium efficacy for preventing and/or treating skin lipid peroxidation to skin. An OPF of from about 10 to about 30 may indicate that the leave-on personal care composition has a low efficacy for preventing and/or treating skin lipid peroxidation to skin.

The skin model may be any suitable skin model, such as pig skins. The skin model may be washed and/or rinsed prior to testing. The leave-on personal care composition may be tested in parallel or with a control leave-on personal care composition. The control leave-on personal care composition may be water. In another example, the control leave-on personal care composition may be a comparative leave-on personal care composition, such as a comparative commercial leave-on personal care composition.

To predict the efficacy of the leave-on personal care composition for preventing lipid peroxidation of skin, the skin models may be contacted with the leave-on personal care composition and subsequently exposed to skin pollution, such as ozone. It should be appreciated that the leave-on personal care composition may remain on the skin model during testing.

Exposing the skin models to skin pollution may include disposing the skin models in a CH-1 ozone chamber (Model 106-L) commercially available from Oxidation Technologies, LLC. The skin models may be exposed to skin pollution for a time and an amount sufficient to generate MDA in and/or on skin. For example, the skin models may be exposed to about 100 ppb of ozone for about 1 hour to generate MDA.

Contacting the leave-on personal care composition with the skin may include contacting a predetermined amount of the test and/or control leave-on personal care composition with respective skin models for a predetermined amount of time. For example, about 50 mg of the test and/or control leave-on personal care composition may be contacted with respective skin models in an even thin coating prior to exposing the skin models to skin pollution.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The efficacy of a test or exemplary personal care composition (1) for preventing pollution damage to skin or its ability to provide anti-pollution benefits to skin was evaluated and compared to a control or comparative personal care composition (2) having anti-pollution benefits. The test (1) and control (2) personal care compositions were prepared by combining the ingredients/components according to Table 1. It should be appreciated that the total concentration of surfactants in the test personal care composition (1) and the control personal care composition (2) was about 9.65 wt % and about 9.99 wt %, respectively. As such, any distinctions between the test (1) and control (2) personal care compositions may be attributed to the respective combination or selection of surfactants instead of respective amount of surfactants contained in each of the total surfactant level of each of the test (1) and control (2) personal care compositions.

TABLE 1

Test (1) and Control (2) Personal Care Compositions

| COMPONENT | TEST (1) (% WEIGHT) | CONTROL (2) (% WEIGHT) |
| --- | --- | --- |
| Water | Balance | Balance |
| Cocamidopropyl Betaine (30% Soln) | 20.00 | 5.80 |
| Sodium (C14-16) Olefin Sulfonate (40% Soln) | 8.90 | — |
| Sodium Laureth Sulfate (70% Soln) | — | 10.00 |
| Coco-Glucoside (50% Soln) | — | 2.50 |
| Lactic Acid | 4.02 | 1.10 |
| Glycerin | 5.10 | 5.00 |

TABLE 1-continued

Test (1) and Control (2) Personal Care Compositions

| COMPONENT | TEST (1) (% WEIGHT) | CONTROL (2) (% WEIGHT) |
| --- | --- | --- |
| Preservative | 0.53 | 1.67 |
| Thickener | 0.13 | — |
| Excipients | 1.50 | 5.7 |

To test the efficacy of the test (1) and control (2) personal care compositions for preventing pollution damage to skin or their ability to provide anti-pollution benefits to skin, lipid peroxidation of skin was evaluated. Particularly, the amount of lipid peroxidation generated in skin exposed to ozone after treatment with either the test (1) or control (2) personal care compositions was evaluated. The amount of lipid peroxidation present in and/or on the skin was measured with a lipid peroxidation assay kit, which monitored the presence of a biomarker for lipid peroxidation; specifically, the presence of malondialdehyde (MDA), a byproduct of lipid peroxidation. Pig skins were utilized as skin models for each of the test (1) and control (2) personal care compositions. Particularly, two pieces of 4×2 inch defrosted pig skins were cut into four 2×2 inch samples for testing such that the same 4×2 piece was tested with the test (1) and control (2) personal care compositions, respectively. They were randomized such that two of the four 2×2-inch pig skin samples were washed and lathered with about 200 μL of the test personal care composition (1) for about 15 seconds, and the remaining two 2×2-inch pig skin samples were washed and lathered with about 200 μL of the control personal care composition (2) for about 15 seconds. Prior to washing, each of the pig skin samples were pre-wetted with running water for about 2 to about 3 seconds.

After washing the pig skin samples with either the test (1) or the control (2) personal care composition, the pig skin samples were rinsed for about two to about three seconds with tap water maintained at a temperature of 100±5° F. and a flow rate of about 100 mL/s. After rinsing, each of the pig skin samples were exposed to ozone. Particularly, each of the pig skin samples was placed in a CH-1 ozone chamber (Model 106-L) obtained from Oxidation Technologies, LLC. of Inwood, Iowa, and exposed to about 100 ppm ozone for about 30 minutes. After exposing each of the pig skin samples to ozone, MDA was extracted from each of the pig skin samples. Particularly, MDA was extracted from each of the pig skin samples via a cup scrub method where about 500 μL of ethanol was applied twice. Each of the respective 1 mL ethanol samples (from the two 500 μL washes of ethanol) including the extracted MDA was then centrifuged for about 1 minute at about 10,000 RPM to remove any debris.

To quantify the amount of MDA, a calibration curve was first prepared. Particularly, a 20 μM standard solution of MDA was diluted with ethanol to varying concentrations. A 25 ml solution of thiobarbituric acid (TBA) was prepared by mixing one container of TBA powder (provided in the kit) with about 7.5 mL of acetic acid, and about 17.5 mL of deionizied (DI) water. 200 μL of each of the respective MDA dilutions was then contacted with about 600 μL of the TBA solution, incubated at about 95° C. for about 60 min, and cooled in an icebox for about 10 min. 200 μL of the mixture was then pipetted into a well plate in duplicate. Each sample was then measured using a SPECTRAMAX M5, obtained from Molecular Devices, LLC. of San Jose, Calif. Specifically, each of the samples was excited at a wavelength of about 532 nm and emission was measured at a wavelength of about 553 nm. The measured emission intensity of each of the samples and the corresponding concentration of the dilute MDA solution were then utilized to prepare the calibration curve.

To quantify the amount of MDA extracted from each of the pig skin samples, about 200 μL of the centrifuged MDA samples obtained from the cup scrub method was contacted with about 600 μL of the TBA solution, incubated at about 95° C. for about 60 min, and cooled in an icebox for about 10 min. Similar to the samples prepared for the calibration curve, about 200 μL of the mixture was then pipetted into a well plate in duplicate. Each sample was then measured using a SPECTRAMAX M5. Specifically, each of the samples was excited at a wavelength of about 532 nm and emission was measured at a wavelength of about 553 nm. The measured emission intensity of each of the samples was then utilized to determine the amount of MDA in each of the samples extracted from the pig skins using the calibration curve. The amount of MDA measured from pig skins exposed to ozone after treatment with the test (1) and control (2) personal care compositions is summarized in Table 2. Statistical significance was determined using a two-tailed, two sample equal variance T-test.

TABLE 2

MDA Measured from Pig Skin after Treatment Treated with Test (1) and Control (2) Personal Care Compositions Before and Subsequent Exposure to Ozone.

| SAMPLE | MDA mole per unit area (nmol/cm$^2$) | | Average | Std Dev |
|---|---|---|---|---|
| TEST (1) | 3.67 | 3.11 | 3.39 | 0.39 |
| CONTROL (2) | 6.30 | 6.00 | 6.15 | 0.21 |

OPF of Test (1) for preventing skin pollution damage = 45%

As illustrated in Table 2, relatively less MDA was measured in the pig skins treated with the test personal care composition (1) than the pig skins treated with the control personal care composition (2). Specifically, a decrease in MDA of about 45% was observed between the control personal care composition (2) and the test personal care composition (1). As discussed above, MDA is a byproduct for lipid peroxidation, which is a marker for pollution. As such, it should be appreciated that the test personal care composition (1) including the combination of cocamidopropyl betaine and the olefin sulfate surprisingly and unexpectedly prevented pollution damage to skin when exposing the skin to ozone. The OPF value of the test personal care composition (1) was calculated relative to the control personal care composition (2). An OPF of about 49% was observed.

Example 2

The efficacy of the test (1) and control (2) personal care compositions prepared in Example 1 for removing pollution damage in and/or on skin or its ability to provide pollution healing properties to skin was evaluated. Pig skins were utilized as skin models for each of the test (1) and control (2) personal care compositions. Particularly, two pieces of 4×2 inch defrosted pig skins were cut into four 2×2 inch samples for the two samples cut from the same piece to be treated with the test (1) and control (2) personal care compositions. Each of the pig skin samples was then placed in a CH-1 ozone chamber (Model 106-L) and exposed to about 100 ppm ozone for about one hour, which caused the pig skins to produce MDA.

After exposure to ozone, the four 2×2-inch pig skin samples were randomized and two of the four 2×2-inch pig skin samples were washed and lathered with about 200 μL of the test personal care composition (1) for about 15 seconds, and the remaining two 2×2-inch pig skin samples were washed and lathered with about 200 μL of the control personal care composition (2) for about 15 seconds. After washing, the test (1) or control (2) personal care compositions remained on the respective pig skins for about 60 seconds before rinsing under tap water. Particularly, each of the 2×2-inch pig skin samples was then rinsed for about two to about three seconds with tap water maintained at a temperature of 100±5° F. and a flow rate of about 100 mL/s.

The MDA was then extracted from each of the pig skin samples via a cup scrub method where about 500 μL of ethanol was applied twice. Each of the respective 1 mL ethanol samples (from the two 500 μL washes of ethanol) including the extracted MDA was then centrifuged for about 1 minute at about 10,000 RPM to remove debris. MDA from each of the samples was measured similar to Example 1. The amount of MDA measured from the pig skins exposed to ozone before treatment with the test (1) and control (2) personal care compositions is summarized in Table 3. Statistical significance was determined using a two-tailed, two sample equal variance T-test.

TABLE 3

MDA Measured from Pig Skin after Treatment Treated with Test (1) and Control (2) Personal Care Compositions After Subsequent to Exposure to Ozone

| SAMPLE | MDA mole per unit area (nmol/cm$^2$) | | Average | Std Dev |
|---|---|---|---|---|
| TEST (1) | 2.76 | 2.30 | 2.53 | 0.33 |
| CONTROL (2) | 3.88 | 3.71 | 3.80 | 0.12 |

OPF of Test (1) for removing/treating skin pollution damage = 33%

As illustrated in Table 2, relatively less MDA was measured in the pig skins treated with the test personal care composition (1) than the pig skins treated with the control personal care composition (2). Specifically, a decrease in MDA of about 33% was observed between the control personal care composition (2) and the test personal care composition (1). As discussed above, MDA is a byproduct for lipid peroxidation, which is a marker for pollution. As such, it should be appreciated that the test personal care composition (1) including the combination of cocoamidopropyl betaine and the olefin sulfate surprisingly and unexpectedly reduced, removed, or otherwise treated pollution damage in skin exposed to ozone. An OPF of about 49% was observed.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A method for preventing lipid peroxidation of skin, the method comprising:

contacting a personal care composition comprising a cosmetically acceptable carrier and a surfactant system comprising at least one amphoteric surfactant and at least one anionic surfactant with the skin;

wherein the at least one amphoteric surfactant is a betaine-based surfactant selected from the group consisting of cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, lauryl-bis-(2-hydroxypropyl)-carboxyethyl betaine, and combinations thereof;

wherein the at least one anionic surfactant comprises an alpha olefin sulfonate, and wherein the alpha olefin sulfonate comprises from about 8 to about 20 carbon atoms per molecule, or from about 14 to about 16 carbon atoms per molecule;

wherein the carrier comprises a thickener, wherein the thickener comprises a polymer, wherein the polymer is poloxamer poly(ethylene glycol)-poly(propylene glycol)-poly(ethylene glycol) block copolymer (PEG-PPG-PEG);

wherein the at least one amphoteric surfactant is present in an amount of from about 5 weight % to about 7 weight %, based on a total weight of the personal care composition; and exposing the skin to pollution, wherein the personal care composition prevents lipid peroxidation of the skin.

2. A method for treating lipid peroxidation of skin, the method comprising contacting a personal care composition comprising a cosmetically acceptable carrier and a surfactant system comprising at least one amphoteric surfactant and at least one anionic surfactant with the skin, wherein the at least one amphoteric surfactant is a betaine-based surfactant selected from the group consisting of cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, lauryl-bis-(2-hydroxypropyl)-carboxyethyl betaine, and combinations thereof;

wherein the at least one anionic surfactant comprises an alpha olefin sulfonate, and wherein the alpha olefin sulfonate comprises from about 8 to about 20 carbon atoms per molecule, or from about 14 to about 16 carbon atoms per molecule;

wherein the carrier comprises a thickener, wherein the thickener comprises a polymer, wherein the polymer is poloxamer poly(ethylene glycol)-poly(propylene glycol)-poly(ethylene glycol) block copolymer (PEG-PPG-PEG);

wherein the at least one amphoteric surfactant is present in an amount of from about 5 weight % to about 7 weight %, based on a total weight of the personal care composition; and wherein contacting the personal care composition with the skin reduces lipid peroxidation in and on the skin after exposing the skin to pollution.

3. The method according to claim 1, wherein the at least one amphoteric surfactant comprises cocamidopropyl betaine.

4. The method according to claim 1, wherein the at least one anionic surfactant comprises sodium C14-16 alpha olefin sulfonate.

5. The method according to claim 1, wherein the at least one amphoteric surfactant is present in an amount of about 6 weight %, based on a total weight of the personal care composition.

6. The method according to claim 1, wherein the at least one anionic surfactant is present in an amount of from about 1 weight % to about 6 weight %, or of from about 2 weight % to about 5 weight %, or of from about 3 weight % to about 4 weight %, based on a total weight of the personal care composition.

7. The method according to claim 1, wherein the at least one amphoteric surfactant and the at least one anionic surfactant are present in a weight ratio of from about 0.5:1 to about 3:1, or of from about 1.5:1 to about 2:1, or of about 1.7:1.

8. The method according to claim 1, wherein the surfactant system is present in an amount of from about 2 weight % to about 20 weight %, or of from about 4 weight % to about 16 weight %, or of from about 8 weight % to about 12 weight %, or of about 10 weight %, based on a total weight of the personal care composition.

9. The method according to claim 1, wherein the personal care composition consists essentially of the carrier and the surfactant system, and the surfactant system consists essentially of the at least one amphoteric surfactant and the at least one anionic surfactant.

10. The method according to claim 1, wherein the personal care composition is free of sulfate-containing surfactants.

11. The method according to claim 1, wherein the personal care composition is free of sodium lauryl sulfate (SLS), ammonium lauryl sulfate (ALS), sodium laureth sulfate (SLES), ammonium laureth sulfate (ALES), or combinations thereof.

12. The method according to claim 1, wherein the personal care composition is free of coco-glucoside, salt thickeners, or combinations thereof.

13. The method according to claim 1, wherein the personal care composition has a pH of from about 3.5 to about 5.5, or of from about 4 to about 5, or of about 4.5.

* * * * *